US006666819B2

(12) United States Patent
Heine et al.

(10) Patent No.: US 6,666,819 B2
(45) Date of Patent: Dec. 23, 2003

(54) LARYNGOSCOPE

(75) Inventors: Helmut A. Heine, Herrsching (DE); Gerhard Guegel, Diessen (DE); Dirk Schade, Penzberg (DE); Otto H. Schmidt, Herrsching (DE); Anton Schneider, Munich (DE)

(73) Assignee: Heine Optotechnik GmbH & Co. KG, Herrsching (DE)

( * ) Notice: Subject to any disclaimer, the term of this patent is extended or adjusted under 35 U.S.C. 154(b) by 82 days.

(21) Appl. No.: 10/002,113

(22) Filed: Dec. 5, 2001

(65) Prior Publication Data

US 2002/0068854 A1 Jun. 6, 2002

(30) Foreign Application Priority Data

Dec. 6, 2000 (DE) .......................................... 100 60 645
May 23, 2001 (DE) .......................................... 101 25 389

(51) Int. Cl.[7] .............................................. A61B 17/00
(52) U.S. Cl. ....................................... 600/199; 600/193
(58) Field of Search ................................ 600/185, 188, 600/191, 193, 199, 200, 245

(56) References Cited

U.S. PATENT DOCUMENTS

| | | | | |
|---|---|---|---|---|
| 3,592,199 A | * | 7/1971 | Ostensen | |
| 3,826,248 A | * | 7/1974 | Gobels | |
| 4,517,964 A | * | 5/1985 | Upsher | |
| 4,565,187 A | * | 1/1986 | Soloway | |
| 4,570,614 A | * | 2/1986 | Bauman | |
| 5,036,835 A | * | 8/1991 | Filli | |
| 5,060,633 A | * | 10/1991 | Gibson | |
| 5,529,570 A | * | 6/1996 | Storz | 600/199 |
| 6,013,026 A | * | 1/2000 | Krauter et al. | 600/193 |
| 6,213,937 B1 | * | 4/2001 | Vivenzio | 600/199 |
| 6,354,993 B1 | * | 3/2002 | Kaplan et al. | 600/188 |

FOREIGN PATENT DOCUMENTS

| | | |
|---|---|---|
| DE | 85 26 662 U1 | 12/1985 |
| DE | 42 43 790 A1 | 3/1994 |
| EP | 0 586 972 B1 | 3/1994 |

* cited by examiner

Primary Examiner—Cary E. O'Connor
(74) Attorney, Agent, or Firm—Birch, Stewart, Kolasch & Birch, LLP

(57) ABSTRACT

A laryngoscope (1) includes a socket (3) that is mountable on a hand grip, a spatula blade (2) that is coupled with the socket (3) and a light guide tube (4) that has proximal and distal end portions, with the proximal end portion of the light guide tube (4) being releasably mounted in a cavity (11) that extends completely through the socket (3) while the distal end portion engages in a snap-in device on the spatula blade (2). The light guide tube (4) has a completely uniform permanent cross section that improves the laryngoscope spatula (1) since the light guide tube (4) can be manufactured and serviced in an uncomplicated manner.

14 Claims, 7 Drawing Sheets

Fig. 8a
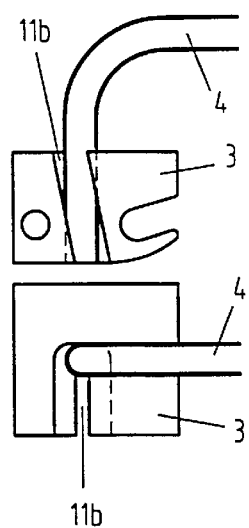
Fig. 8b
Fig. 8c
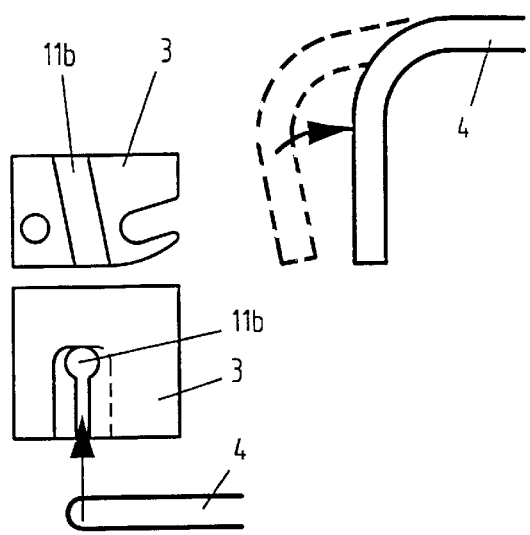
Fig. 8d
Fig. 9a
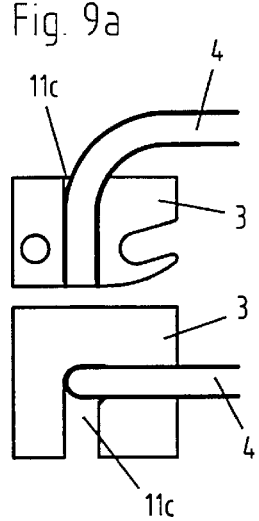
Fig. 9b
Fig. 9c
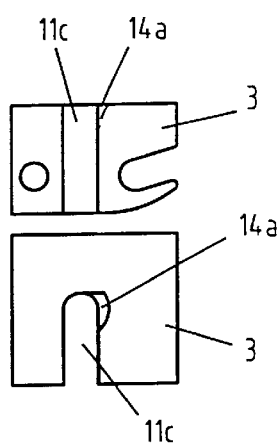
Fig. 9d
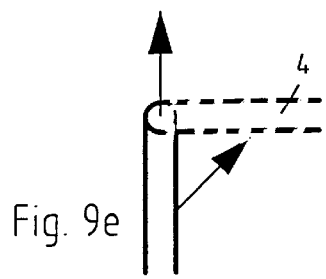
Fig. 9e

LARYNGOSCOPE

BACKGROUND OF THE INVENTION

This application claims a priority based on German Applications DE 100 60 645.8, filed on Dec. 6, 2000 and DE 101 25 389.3, filed on May 23, 2001 and the contents of these priority applications are incorporated by reference herein.

This invention concerns a laryngoscope with a socket mountable on a handle, a spatula blade attached to the socket and a light conductor tube having proximal and distal end portions, with the proximal end portion of the light conductor tube being removably mounted in a cavity extending through the socket, while the distal end portion engages in a snapping attachment on the spatula blade.

Laryngoscopes serve particularly for introducing tubes for artificial breathing in air pipes of patients. For illumination of the throat cover area and the vocal chords, apparatus having fiber optic light guides are preferred. So that durability of the entire laryngoscope spatula is not determined by the relatively short lifespan of the light guides contained therein, laryngoscope spatulas with changeable light guide parts have been developed. These have the advantage that if, because of aging, light transmission of the light guide bundle falls below a particular threshold, the light guide tube is simply replaced by a new light guide tube. Such a laryngoscope spatula is disclosed in European Patent EP 0 586 972 B1.

According to European Patent EP 0 586 972 B1, a narrow side opening is provided in a socket of a laryngoscope spatula into which a light guide tube can be laterally placed. A sideward release of the light guide tube is, in this regard, prevented in that an enlarged area of the light guide tube engages in an enlarged area of the opening, with a breadth of the side opening being smaller than the breadth of the enlarged area of the light guide tube. The light guide tube has, in this regard, at an end of the enlarged area a tube flange, which serves as a stop during an insertion movement. Such an embodiment of the light guide tube is installed, according to European Patent EP 0 586 972 B1, by one first moving a small breadth area sidewardly through the small side opening and then inserting it lengthwise until engagement of the tube flange, and then by pivoting approximately 90 degrees to fix it in an end position. a proximal facing end of the light guide tube extends, in this regard, out from the socket.

It is detrimental that for such a laryngoscope spatula the construction of the part of the light guide tube to be mounted in the side socket opening, which has a step-wise structure with three breadths, is so expensive; and also, that there is a relatively complicated learning-intensive procedure for mounting the light guide tube. Further, the sensitive proximal facing end of the light guide, which extends out of the socket, is exposed to mechanical loads during fabrication and disassembly of the structure, which could lead to a damaging of the facing surface of the light guide.

It is an object of this invention to provide a laryngoscope with a changeable light guide tube of the type set forth in the opening paragraph above that avoids the disadvantages set forth above and therefore allows a particularly uncomplicated replacement procedure for replacing the light guide tube.

SUMMARY OF THE INVENTION

According to principles of this invention, the light guide tube has, throughout its length, a substantially uniform permanent breadth, which allows a particularly uncomplicated fabrication of the light guide tube. This also allows the proximal facing end of the light guide to be held within the socket, which assures better mechanical protection for the facing end. Additional advantages and advantageous embodiments of a laryngoscope according to this invention are described and claimed herein.

BRIEF DESCRIPTION OF THE DRAWINGS

Embodiments of the invention are described in more detail using the following drawings. In the drawings:

FIG. 2a is a side view of the distal end of a laryngoscope of this invention with a snapped-in light guide tube (embodiment 1);

FIG. 2b is a plan view of a spatula portion of the device of FIG. 2a;

FIG. 2c is a cross-sectional view taken on line II—II in FIG. 2a;

FIG. 3a is a side view of the distal end of a laryngoscope of this invention with a snapped-light guide tube (embodiment 2);

FIG. 3b is a plan view of a spatula portion of the device of FIG. 3a;

FIG. 3c is a cross-sectional view of the spatula portion taken on line III—III in FIG. 3a;

FIG. 4a is a side view of a distal end of a laryngoscope of this invention with a snapped-in light guide tube (embodiment 3);

FIG. 4b is a plan view of a spatula portion of the device of FIG. 4a;

FIG. 4c is a cross-sectional view of the spatula portion taken on line IV—IV in FIG. 4a;

FIG. 5a is a side view of a distal end of a laryngoscope of this invention with a snapped-in light guide tube (embodiment 4);

FIG. 5b is a plan view of a spatula portion of the device of FIG. 5a;

FIG. 5c is a cross-sectional view of the spatula portion taken on line V—V in FIG. 5a;

FIG. 5d is a side view of the distal end of a laryngoscope of this invention with a snapped-in light guide tube (embodiment 5);

FIG. 5e is a plan view of a spatula portion of the device of FIG. 5d;

FIG. 5f is a cross-sectional view taken on line V'—V' in FIG. 5d;

FIG. 6b is a plan view of the socket with the light guide tube of FIG. 6a;

FIG. 8a is a side view of a socket with an inserted light guide tube (variant 2);

FIG. 8b is a plan view of the socket with the light guide tube of FIG. 8a;

FIG. 8c is an exploded side view illustrating a bending pivoting movement of the light guide tube upon its being mounting into the socket (variant 2);

FIG. 8d is a plan exploded view of the socket with the light guide tube of FIG. 8c;

FIG. 9a is a side view of a socket with an inserted light guide tube (variant 3);

FIG. 9b is a plan view of the socket with the light guide tube of FIG. 9a;

FIG. 9c is a side view of the socket (variant 3);

FIG. 9d is a plan view of the socket (variant 3);

FIG. 9e is a view illustrating a pivotal movement of the light guide tube upon its mounting in the socket (variant 3);

FIG. 10b is a plan view of the socket with the inserted light guide tube of FIG. 10a;

FIG. 11b is a plan view of the socket with the light guide tube of FIG. 11a;

DETAILED DESCRIPTION OF THE INVENTION

Figure 1A:
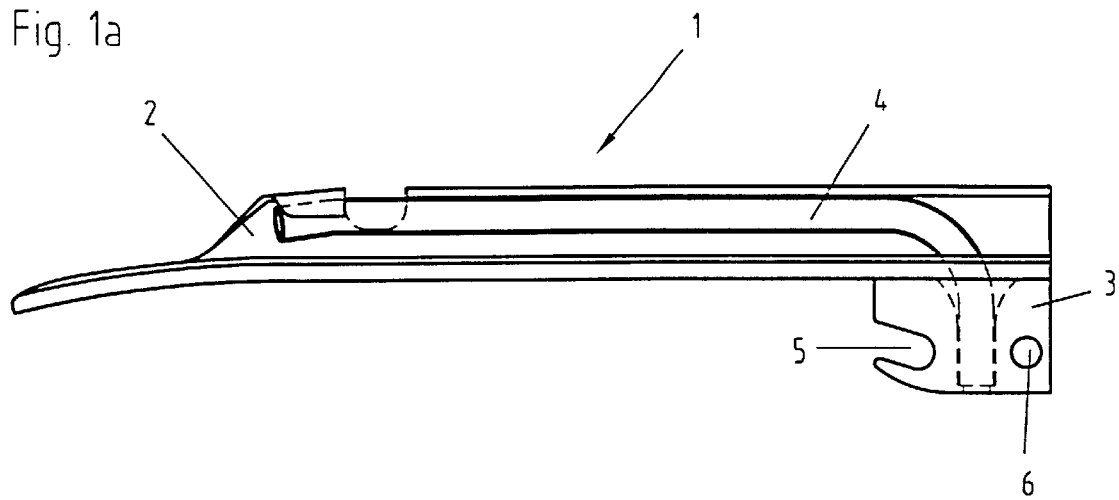
FIG. 1a is a side view of a general laryngoscope of this invention with a light guide.
Figure 1B:
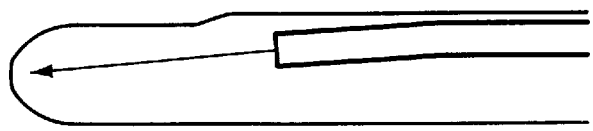
FIG. 1b is a simplified plan view of the distal end of a laryngoscope with a bowed light guide tube.
Figure 1C:
FIG. 1c is a simplified plan view of a distal end of a laryngoscope with a skewed-angled cut light guide tube.

FIG. 1a shows a laryngoscope 1 that includes a spatula blade 2 and a socket 3 with a light guide tube 4 mounted in a snap-in catch. The socket 3 that is affixed to the proximal end of the spatula blade 2 serves as a base part of the laryngoscope 1 that is fastened by a cavity 5 to a handle with a battery and a miniature incandescent light (not shown) and is affixed therein with the help of an indexing, or snapping, ball 6. The light guide tube 4 is formed as a fiberglass bundle covered with a metallic mantel that is elastically springy, and accordingly bowed. The light guide tube 4 extends directly adjacent to and substantially parallel to a side portion of the spatula blade 2. An optimal illumination of an operational area at the distal end of the laryngoscope 1 therefore requires a change in a dispersion direction of a light beam, which can result in the suggested variants of FIGS. 1b and 1c. The light guide tube 4 can either be laterally bowed in a direction away from the spatula blade 2, as is shown in FIG. 1b wherein it has a square cut distal facing end, or the distal facing end can be cut at a skewed angle as is shown in FIG. 1c so that it causes a light deflection at the distal facing end of the light guide tube. It should be noted that the embodiments of the distal end of the light guide tube shown in FIGS. 1b and 1c can be used in all of the embodiments disclosed herein.

Figure 2:
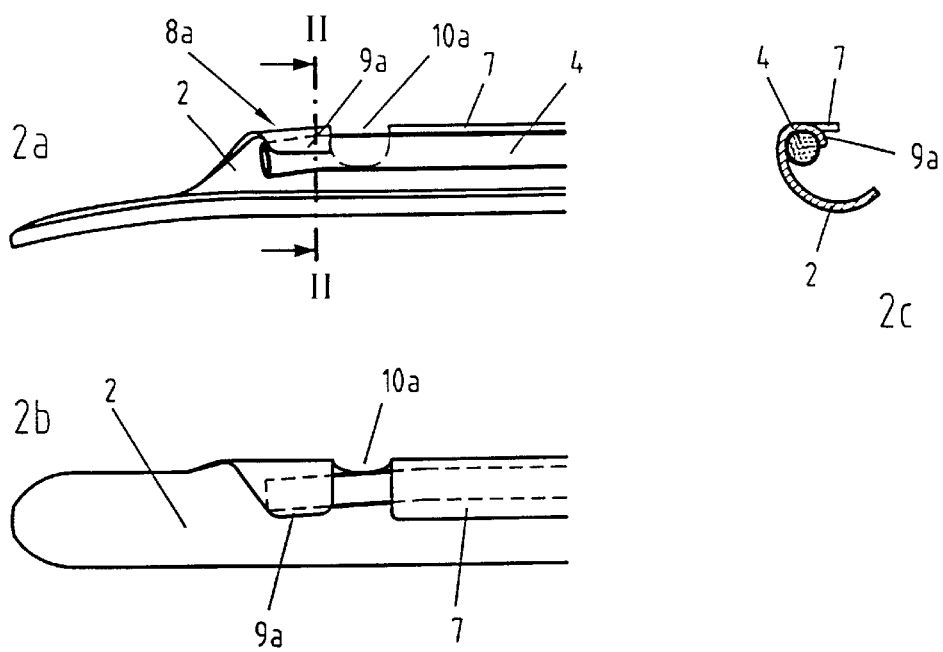

FIGS. 2a through 2c depict a first embodiment of attachment of the light guide tube 4 at the distal end of the laryngoscope spatula 1. As can be seen in FIG. 2c, the spatula blade 2 has a clamp-like cross section with a flanged spatula backside 7. The distal end portion of the light guide tube 4 is therefore affixed in a snap-in catch 8a formed by a fold-back 9a at a distal edge of the spatula backside 7. Because of the elastic springy characteristics of the light guide tube 4, it can be snapped under the fold-back by a light finger pressure. For unsnapping the light guide tube 4, a grip-trough opening 10a is provided in the fold-back 9a that forms the snap-in catch at the spatula backside 7.

FIGS. 3a through 3c show a second snap attachment variant for the light guide tube 4. Also here the snap-in attachment 8b is formed by a fold-back 9b of the spatula backside 7 near the distal end of the laryngoscope spatula 1. The elastically springy light guide tube 4, in this embodiment, is unlatched by a light finger pressure on the distal end of the light guide tube 4 that extends out from under the spatula backside 7.

FIGS. 4a through 4c show a distal end of the laryngoscope 1 that has a third snap attachment variant according to this invention. In this case, the affixing is accomplished by a bead 9c that is positioned close to the distal end of the laryngoscope, arranged in the lower inside portion of the spatula backside 7. Also here the affixing is accomplished through the elastically springy characteristics of the light guide tube 4 that is snapped in by a horizontal pivoting movement after overcoming the part 9c that is formed out of the plane of the spatula backside 7. The unlatching can be accomplished in this embodiment through a grip-trough opening 10c arranged distal to the snap-in catch 8c at a bend area of the spatula backside 7. In this embodiment, a light finger pressure on the light guide tube 4 through the grip-trough opening 10c is sufficient to achieve unlatching.

Figure 3:
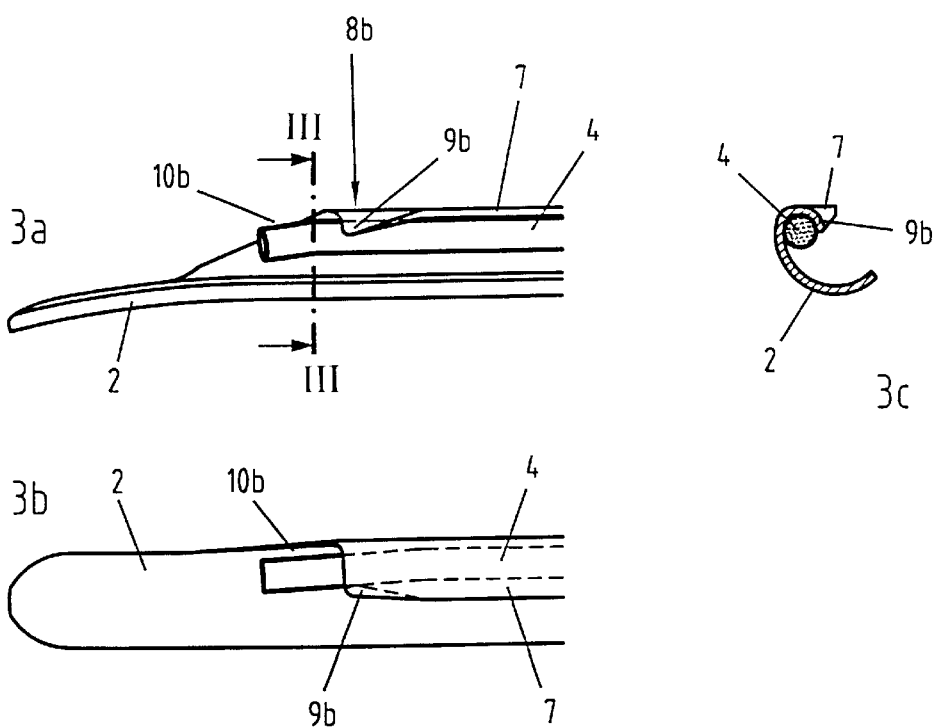
Figure 4:
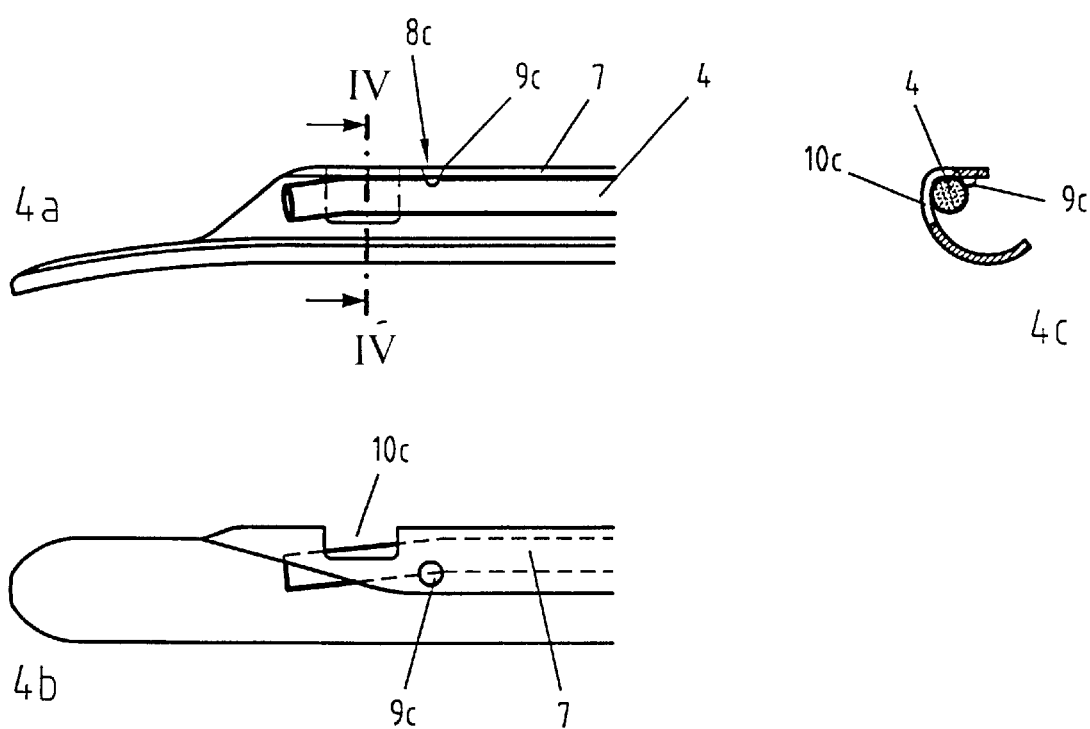
Figure 5:
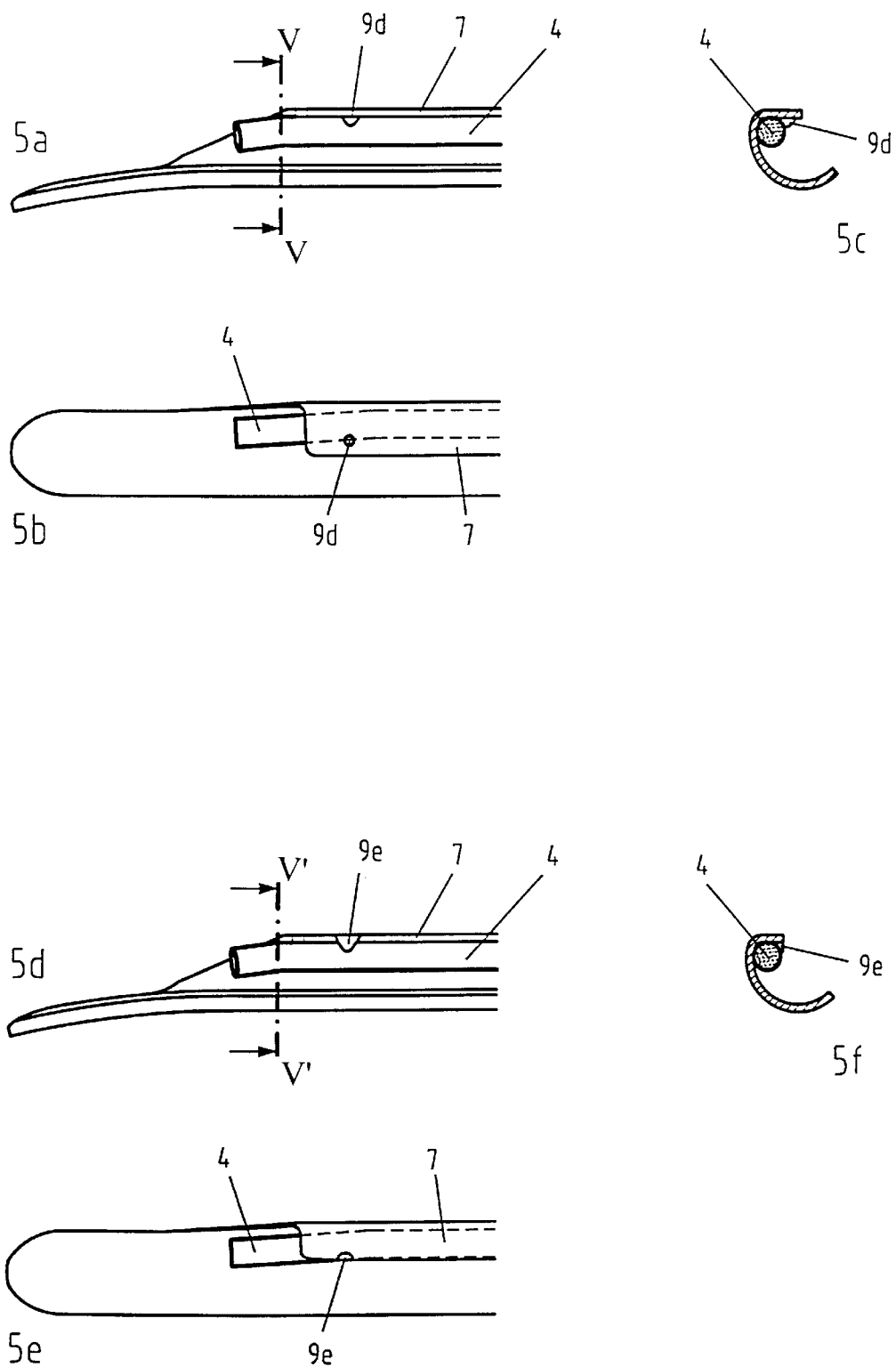

FIGS. 5a through 5c show a fourth snapping variant of the distal end of the laryngoscope 1 that represents a cross between the variants shown in FIGS. 3 and 4. Similarly as in FIGS. 4a through 5c, the affixing is accomplished via a bead 9d which lies near the distal end of the laryngoscope 1 and which is arranged in the lower portion of the spatula backside 7. The affixing comes about because of the elastically springy characteristics of the light guide tube 4 that snaps in upon a horizontal pivoting movement following overcoming the part 9d of the spatula backside 7 that is out of the plane of the spatula backside 7. The unlatching can, in this embodiment, be caused by a light finger pressure on the end of the light guide tube 4 extending out from under the spatula backside 7.

Upon the affixing of the light guide tube 4 under the spatula backside 7, a contacting of the light guide tube 4 with an area of the spatula backside 7 in front of the bead 9d by a person using the laryngoscope can be perceived as a final affixed position. FIGS. 5d through 5f show a fifth snapping attachment variant of the distal end of the laryngoscope 1 in which a danger of confusing a final attachment position of the light guide tube 4 under the spatula backside 7 is ruled out because of rubbing between these two parts, or because of an optical partial covering of the light guide tube 4 by the spatula backside 7 in front of the bead 9c. This is achieved because a lowest position of the bead 9e simultaneously serves as the first and only obstacle in the affixing path of the light guide tube 4. The spatula backside 7 extends to converge in a wedge-shape in the direction of the distal end with the fold-back edge intersecting the lowest position of the bead 9e. Because of the elastically springy characteristics of the light guide tube, after overcoming the part 9e extending out of the plane of the spatula backside 7 a final arresting is accomplished by a light finger pressure on the distal end of the light guide tube 4. The uncoupling can be caused in this embodiment by a light finger pressure and a rotational, pivotal movement of the light guide tube 4 in an opposite direction. This embodiment relates to each of the four previously described snap-in variations. This variant has the substantial benefit that the "cutaway" portion, contrary for example to FIGS. 5a–5c, of the spatula backside is not an obstacle to viewing in the throat of a patient.

Figure 6A:
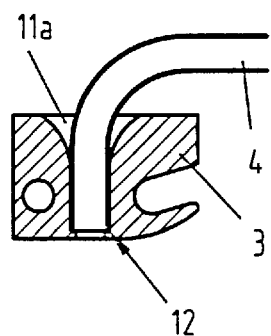
FIG. 6a is a side view of a socket for this invention with an inserted light guide tube (variant 1)
Figure 6B:
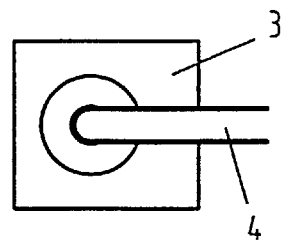

FIGS. 6a and 6b show the socket 3 of the laryngoscope 1 with an inserted proximal end of the light guide tube 4 in accordance with a first variant of the attachment of the proximal end of the light guide tube 4 in a guided-in catch. At the proximal end of the light guide tube 4 there is preferably a shape without a cross-sectional change. A cavity 11a having a form corresponding to that of the light guide tube 4 and extending through the socket 3 thereby prevents a sideward falling out of the light guide tube 4 and assures a stable seating position of the light guide tube 4 in the socket 3. As can be seen in FIG. 6a, the proximal end of the light guide tube 4 is positioned at a cross sectional constriction 12, that amounts to a step transition of the cross section of the cavity 11a from a first cross section that corresponds substantially to the cross section of the light guide tube 4 to a smaller cross section. The smaller cross section can be so chosen that the light guides are not covered within the light guide tube 4. Because the proximal facing end of the light guide tube 4 is positioned within the cavity 11a of the socket 3, a mechanical protection of this sensitive facing end is assured.

Figure 7A:
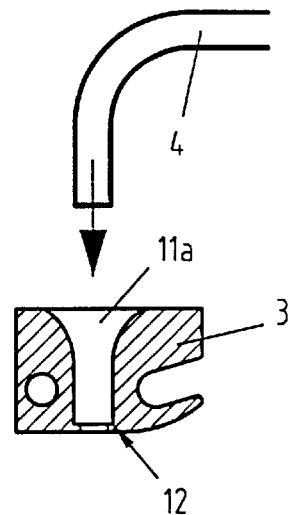
FIG. 7a is an exploded, partially cross-sectional, view illustrating an insertion movement of a light guide tube into a socket (variant 1)
Figure 7B:
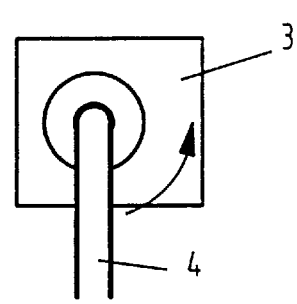
FIG. 7b is a plan view illustrating a pivotal movement of the light guide tube in the socket (variant 1)
Figure 10A:
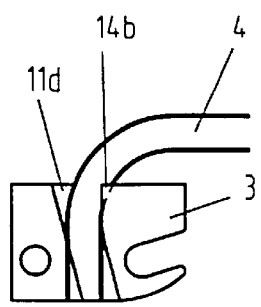
FIG. 10a is a side view of a socket with an inserted light guide tube (variant 4)
Figure 10B:
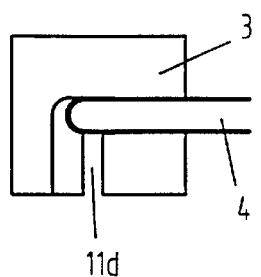
Figure 10C:
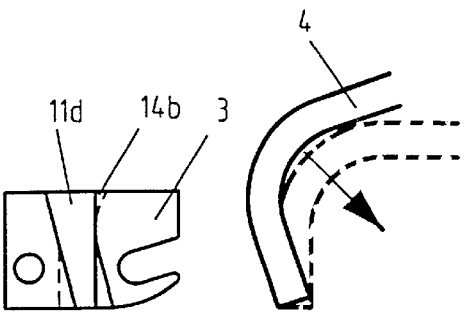
FIG. 10c is a side exploded view illustrating a bending pivoting movement of the light guide tube upon its mounting in the socket (variant 4)
Figure 10D:
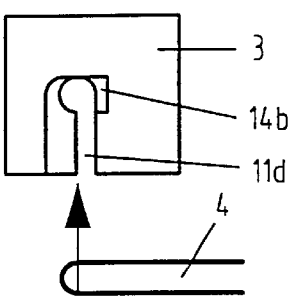
FIG. 10d is a plan exploded view of the socket with the light guide tube of FIG. 10c.
Figure 11A:
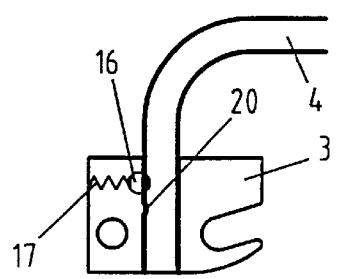
FIG. 11a is a side view of a socket with an inserted light guide tube (variant 5)
Figure 11B:
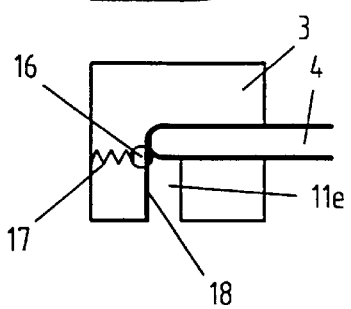
Figure 11C:
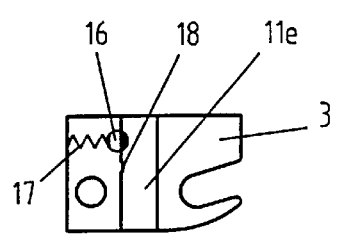
FIG. 11c is a side view of the socket (variant 5)
Figure 11D:
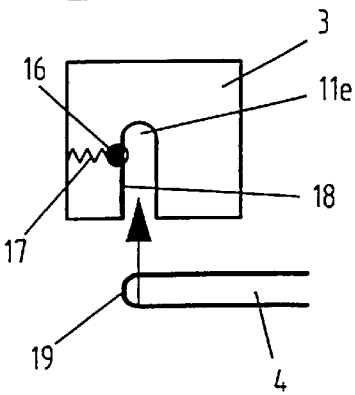
FIG. 11d illustrates a movement of the light guide tube upon its being mounted in the socket (variant 5).

FIGS. 7a and 7b show a preferred manner in which the light guide tube 4 is placed and affixed in the laryngoscope 1 of the embodiment of FIGS. 6a and 6b. The first step includes insertion of the proximal end of the light guide tube 4 in the socket cavity 11 until contact against the cross-sectional constriction 12. Thereafter, a rotational movement of the light guide tube 4 to below the spatula backside 7 affixes the light guide tube 4. The rotational movement can also be less than 90 degrees if the light guide tube 4 is mounted at an acute angle to the spatula blade 2, which is possible according to this invention.

This invention is not limited in its embodiments to the above given shape of the cross-sectional constriction 12. Rather, many different variations will occur to those of ordinary skill in the art that basically differ from the above described solution by making use of other types of cross-sectional changing shapes for the cross-sectional constriction (for example, conical, round and so forth).

For each of the above described embodiments for affixing the light guide tube 4 to the distal end of the laryngoscope 1, the below described variations of placing the proximal end of the light guide tube 4 in the socket 3 can also be used.

FIGS. 8a through 8d show a further embodiment for attaching the proximal end of the light guide tube 4, without the cross sectional change, in the socket 3. The socket 3 has, in this regard, a side opening 11b whose inclination angle to vertical changes from the edge area to the middle of the socket 3. The angle between the access of the opening 11b and a normal to the socket in its operational position has thereby a maximum value at the edge, or outer surface, area of the socket 3 and is minimal or equal to zero in the center of the socket 3. An opposite arrangement in which the minimal angle is in the edge area of the socket and the maximum angle is in the center of the socket 3 is also possible. Upon mounting the light guide tube 4 in the opening 11b of the socket 3 the light guide tube 4 makes a pivot bending movement which is required by the change in the inclination angle of the opening 11b, as can be seen in FIG. 8c. In a mounted position (see FIG. 8b) the light guide tube 4 is held tightly in the middle of the socket 3 by a protrusion caused by angling the side opening 11b, on the one hand, and by the affixing of the distal end of the light guide tube 4, on the other hand.

A further embodiment of the attachment of the light guide tube 4 in the socket 3 of the laryngoscope 1 is shown in FIGS. 9a through 9d. A characteristic of this embodiment is the presence of a cavity 14a in an upper edge area of the straight side opening 11c near the middle of the socket 3. The cavity 14a, in this regard, has a geometric shape that form-locks with a portion of the light guide tube 4 lying on the socket 3 that, after a sideward insertion into the opening 11c and a horizontal pivoting (see FIG. 9e), is affixed in the socket 3. This embodiment sets a limit on movement of the light guide tube 4 in a mounted position toward the top, for example that the upper edge of the light guide tube 4 lies against the spatula backside 7 or is affixed in the snapping apparatus on the spatula tube 2. In this attached positioned (see FIG. 9b) the light guide tube 4 that engages in the snapping apparatus on the spatula blade (not shown) is, with the help of the cavity 14a, prevented from falling out sidewardly through the opening 11c.

FIGS. 10a through 10d show a further embodiment of the attachment of the light guide tube 4 in the socket 3 that is a cross between the embodiments depicted in FIGS. 8a–8d and FIGS. 9a–9d. Similarly as in FIGS. 8a through 8d, the affixing of the light guide tube 4 and the socket 3 is carried out by insertion of the light guide tube 4 in a side opening 11d that has an inclination angle that changes along a path through the socket 3. Further, the light guide tube 4, similarly as in FIGS. 9a through 9d, is fixed by a cavity 14b in the opening 11d. Also, here the cavity 14b is geometrically shaped to lock with a corresponding part of the light guide tube 4.

The attachment of the light guide tube 4 and socket 3 shown in the embodiment of FIGS. 11a through 11d includes a snapping ball 16 provided in the socket 3 with an elastic spring 17 which prevents the light guide tube 4 from falling out of the opening 11e sidewardly. This embodiment allows a particularly uncomplicated mounting and affixing of the light guide tube 4 in the socket 3 by a simple sideward insertion movement (see FIG. 11d) and thereafter a light finger pressure in the insertion direction without a rotation of the light guide tube 4 whose displacement in the vertical direction is prevented by a horizontally extending protrusion 18 in the sideward opening 11e and a correspondingly-shaped cavity 20 in the light guide tube 4. A flattened surface 19 at the proximal end of the light guide tube 4 allows one to completely eliminate a snapping apparatus on the spatula blade, which leads to a further simplification of the construction and therefore to a corresponding reduction in manufacturing costs.

We claim:

1. Laryngoscope having a socket mountable on a hand grip, a spatula blade coupled to the socket having a spatula backside, and a light guide tube with proximal and distal end portions, the proximal end portion of the light guide tube being releasably mounted in a cavity extending through the socket and the distal end portion thereof engaging in a snap-in device on the spatula blade, wherein the light guide tube has substantially a constant cross section throughout.

2. Laryngoscope according to claim 1, wherein the cross section of the light guide tube is circular.

3. Laryngoscope according to claim 1, wherein the snap-in device includes a fold-back at a distal edge of the spatula backside, there being a grip-trough opening in the spatula backside proximal to the fold-back for unlatching the light guide tube.

4. Laryngoscope according to claim 3, wherein an outermost portion of the fold-back serves as a first obstacle on an affixing path of the light guide tube.

5. Laryngoscope according to claim 1, wherein the snap-in device includes a fold-back at a distal edge of the spatula backside and the distal end of the light guide tube can be unlatched by finger pressure on an end of the light guide tube extending from under the spatula backside.

6. Laryngoscope according to claim 1, wherein a grip-trough opening is formed in the spatula backside at the edge of the spatula backside for unlatching the light guide tube, and the snap-in device includes a bead in the spatula backside arranged proximal the grip-trough opening.

7. Laryngoscope according to claim 1, wherein the snap-in device has a bead in the spatula backside at a distal edge portion thereof and a distal end of the light guide tube is unlatchable by a finger pressure on its end extending from under the spatula backside.

8. Laryngoscope according to claim 1, wherein the cavity extending through the socket has a cross sectional constriction against which a proximal end of the light guide tube lies.

9. Laryngoscope according to claim 8, wherein the constriction is a step-wise transition of the cross section of the cavity extending through the socket from a first cross section, which substantially corresponds to the cross sectional of the light guide tube, to a smaller cross section.

10. Laryngoscope according to claim 1, wherein a proximal facing end of the light guide tube is within the cavity of the socket.

11. Laryngoscope according to claim 1, wherein the cavity extending through the socket includes a side slot with a variable angle between the slot's entrance and a normal operational position of the slot.

12. Laryngoscope according to claim 1, wherein the cavity extending through the socket has a cavity that is geometrically formed to lock with an engaging part of the light guide tube.

13. Laryngoscope with a socket having a cavity extending completely therethrough that can be mounted on a hand grip, a spatula blade coupled to the socket that has a spatula backside, and a light guide tube having a proximal end portion and a distal end portion, with the proximal end portion of the light guide tube being releasably mounted in the cavity extending completely through the socket, wherein there is at least one protrusion and at least one spring snap-in device provided in the cavity to affix the light guide tube, with the proximal end of the light guide tube being shaped to form fit the cavity, wherein the light guide tube includes a flattened surface at its proximal end portion that is parallel to a mounting direction, which lies against an inner wall of the cavity and thereby prevents a rotational movement of the light guide tube.

14. Laryngoscope according to claim 13, wherein the snap-in device includes a snap-in ball and a prebiased elastic device.

* * * * *